United States Patent
Mekata et al.

(10) Patent No.: US 7,226,579 B1
(45) Date of Patent: Jun. 5, 2007

(54) AEROSOL COMPOSITION

(75) Inventors: Satoshi Mekata, Ibaraki (JP); Masasuke Sakai, Nara (JP)

(73) Assignee: Daizo Co., Ltd. (JP)

( * ) Notice: Subject to any disclaimer, the term of this patent is extended or adjusted under 35 U.S.C. 154(b) by 0 days.

(21) Appl. No.: 10/089,551

(22) PCT Filed: Jul. 31, 2000

(86) PCT No.: PCT/JP00/05100

§ 371 (c)(1),
(2), (4) Date: Jun. 28, 2002

(87) PCT Pub. No.: WO01/25368

PCT Pub. Date: Apr. 12, 2001

(30) Foreign Application Priority Data

| Oct. 1, 1999 | (JP) | ................... 11-281763 |
| Feb. 18, 2000 | (JP) | .................... 2000-040807 |
| Jul. 10, 2000 | (JP) | .................... 2000-208980 |

(51) Int. Cl.
*A01N 25/06* (2006.01)
(52) U.S. Cl. .................. 424/45; 424/43; 424/76.2; 424/405; 424/406
(58) Field of Classification Search ............... 424/405, 424/44, 45, 47
See application file for complete search history.

(56) References Cited

U.S. PATENT DOCUMENTS 2,524,590 A * 10/1950 Boe ............... 516/6
2,803,581 A * 8/1957 Hibbard ............... 424/701
5,055,299 A * 10/1991 Dohara et al. ............... 424/405
5,620,678 A * 4/1997 Burke ............... 424/45
5,792,465 A * 8/1998 Hagarty ............... 424/405

FOREIGN PATENT DOCUMENTS

| CA | 1166374 | | 4/1984 |
| DE | 3138298 | | 6/1982 |
| EP | 0 320 908 B1 | | 7/1991 |
| EP | 0521455 | * | 7/1993 |
| EP | 0888716 | * | 7/1999 |
| EP | 1249482 | * | 10/2002 |
| JP | 57-090078 | | 6/1982 |
| JP | 4-314780 | | 11/1992 |

(Continued)

OTHER PUBLICATIONS

People's Republic of China Office Action dated Apr. 18, 2003.
International Search Report PCT/JP00/05100, mailed on Oct. 17, 2000.

*Primary Examiner*—Neil S. Levy
(74) *Attorney, Agent, or Firm*—Rader, Fishman & Grauer PLLC (57) ABSTRACT

A one-pack aqueous aerosol composition being highly secure against fire and enabling efficient adhesion of an active ingredient. This aerosol composition is a homogeneous one which comprise 10 to 60 wt % of a liquid concentrate consisting of 30 to 90 wt % of an oil such as kerosene, 5 to 50 wt % of a polyhydric alcohol such as diethylene glycol, 1 to 40 wt % of water, and 0.1 to 20 wt % of an active ingredient such as insecticide and not exhibiting any flash point at a pressure of 1 atm and 90 to 40 wt % of a propellant consisting of diethyl ether.

8 Claims, 4 Drawing Sheets

| | FOREIGN PATENT DOCUMENTS | | WO | WO 96/22686 | 8/1996 |
|---|---|---|---|---|---|
| JP | 04-314780 A1 | 11/1992 | WO | WO 01/25368 | 4/2001 |
| JP | 6092841 | 4/1994 | | | |
| WO | WO-94/03056 | 2/1994 | * cited by examiner | | |

AEROSOL COMPOSITION

TECHNICAL FIELD OF THE INVENTION

The present invention relates to an aerosol composition, more specifically, relates to an aerosol composition preferable for an insecticide.

BACKGROUND ART

Aerosol insecticides, generally, consist of an oily concentrate consisting of an effective ingredient (such as an insecticide) and a propellant. Flammable liquefied petroleum gas (LPG) is used for a propellant, thereby causing to high flammability and high ignitability. Therefore, for the purpose of improving safety against fire, such as flammability and ignitability, aerosol insecticides, containing a kerosene solution, dimethyl ether and LPG in a specific proportion, has been applied for a patent (or example, Japanese Unexamined Patent Publication Nos. 1976-67732, 1976-70826, etc.). This satisfies the conditions for the weak flammability (flame length: 45 cm or shorter, lower limit explosion concentration: 0.13 g/L (liter) or higher) in the flammability classification defined by the former Ministry of International Trade and Industry notice No. 557 (Oct. 15, 1965), in a flame length test and an explosion concentration test. When the above-mentioned aerosol insecticide is sprayed, the propellant is vaporized faster than the concentrate as the concentrate is dispersed in a space. Therefore, if the concentrate itself has a flash point, its safety against fire cannot be high. In recent years, in consideration of safety such as ignitability and toxicity against a living body, development of water-based aerosol insecticides is going ahead one after another.

Though such water-based aerosol insecticide become high in safety against fire through using a water-based concentrate, corrosive property is caused to a tinplate-made aerosol container, commonly used for aerosol insecticides, due to the contained water. In addition, an aqueous insecticide ingredient should be selected, but such insecticide ingredient cannot attach effectively to a surface of an oleophilic pest, causing a problem in efficacy. Moreover, drying characteristics becomes worse, resulting in insufficient usability.

As means for solving these problems, a W/O type emulsion aerosol insecticide consisting of an effective ingredient, an oleophilic solvent such as kerosene, an emulsifier, LPG and the like was proposed (for example, Japanese Examined Patent Publication No. 1980-2401, Japanese Patent No. 2855736, etc.). In this insecticide, a water phase is dispersed in an oil phase kerosene and LPG), and thereby water merely contacts directly to the inner surface of the container to prevent corrosion. However, such aerosol product of a W/O type emulsion has problems in stability of emulsion as well as problems of complicated manufacturing processes.

A technological subject of the present invention is to provide a one-component type aerosol composition high in safety against fire, capable of preventing corrosion of the container, and also capable of attaching effectively the effective ingredient to an oleophilic surface.

DISCLOSURE OF THE INVENTION

The aerosol composition according to the present invention is characterized by consisting of a concentrate of 10 to 60 wt % including of an oil ingredient of 30 to 90 wt %, polyol of 5 to 50 wt %, water of 1 to 40 wt % and an effective ingredient of 0.1 to 20 wt % and having no flash point under 1 atmospheric pressure, and a propellant of 90 to 40 wt % including of dimethyl ether, and by that a uniform phase is formed as a whole. Such aerosol composition is preferably prepared with a concentrate consisting of a hydrophilic liquid including of polyol and water and an oleophilic liquid including of an effective ingredient and an oil ingredient, wherein the both liquids separate from each other. As the said effective ingredient, an insecticide can be used.

THE PREFERRED EMBODIMENTS OF THE PRESENT INVENTION

The aerosol composition according to the present invention is, as described above, characterized by consisting of a concentrate of 10 to 60 wt % including of an oil ingredient of 30 to 90 wt %, polyol of 5 to 50 wt %, water of 1 to 40 wt % and an effective ingredient of 0.1 to 20 wt % and having no flash point under 1 atmospheric pressure, and a propellant of 90 to 40 wt % including of dimethyl ether, and by forming a uniform phase.

In such aerosol composition, oil, polyol and water are compounded in the concentrate in a specific proportion, and hence, the concentrate has no flame point under 1 atmospheric pressure to bring a high safety against fire. "Having no flame point" mentioned herein means the case where in the test designated by "Article 1 Paragraph 6, Decree Law with regard to regulation of hazardous materials," flaming is not observed during a period from heating a concentrate under room temperature to boiling. In other words, the concentrate according to the present invention is not the hazardous material because it does not fit to a flammable liquid defined by Remark No. 10, the appended Table, Fire Defense Law in Japan. Consequently, the present invention is not subject to any restriction by the said law in storing and handling as an aerosol product.

Further, although the said concentrate is in a state where the mixture (water-based liquid) consisting of the polyol and water separates from the oily liquid consisting of the effective ingredient and the oil ingredient, the propellant consisting of dimethyl ether is compounded as much as 90 to 40 wt %, so that the aerosol composition forms a uniform phase. When an aerosol composition forms a uniform phase, despite compounding a little water, the concentration of the water in the composition becomes lower than that in any aerosol composition with water dispersed in droplet, resulting in less degree of corrosion of a container.

When the said aerosol composition is sprayed, water and the oil ingredient are separated again. However, the effective ingredient is dissolved in the oil ingredient, and therefore the effective ingredient can be efficiently attached even to objective oleophilic faces for spraying (surfaces of pests).

The said oil ingredient is not only used as a solvent to dissolve the effective ingredient insoluble in water, but also as a ingredient to attach effectively the effective ingredient to objective oleophilic faces for spraying (surfaces of pests). Hydrocarbon, ester oil, silicon, oil and fat and the like are used as such oil ingredient.

Specifically, the hydrocarbon is prepared with one of the following materials: paraffinic aliphatic hydrocarbons such as hexane, heptane, octane, nonane, decane, undecane, dodecane, tridecane, tetradecane, pentadecane, hexadecane, eicosane and pentacosane; isoparaffin aliphatic hydrocarbons such as 2,2,3,3-tetramethyl butane, 2,2-dimethyl hexane, 2,2,3-trimethyl pentane, 2-methyl heptane, 2,2,5-trimethyl hexane, 2,2-dimethyl heptane, 3,3,4-trimethyl hexane, 2-methyl octane, 2-methyl nonane and 2-methyl decane; olefinic aliphatic hydrocarbons such as 1-pentene, 1-hexene, 1-heptene, 1-octene, 1-nonene, 1-decene, 1-undecene, 1-dodecene, 1-tridecene, 1-tetradecene, 1-pentadecene, 1-eicocene and 1-pentacocene; aromatic hydrocarbon such as benzene, octyl benzene, dodecyl benzene and phenyl xylyl ethane; and the mixture thereof, for example, kerosene, paraffin, liquid paraffin, isoper L (brand name), isoper M (brand name), IP Solvent 2028 (brand name), IP Solvent 2835 (brand name), Certrex 60 (brand name), Nisseki Isosol 400 (brand name), Exxon Solvent No. 7 (brand name), Exxol D80 (brand name), Neothiosol (brand name), No. Zero Solvent M (brand name) and No. Zero Solvent H (brand name).

The said ester oil is prepared with such material as isopropyl myristate, cetyl octanoate, octyl dodecyl myristate, isopropyl palmitate, butyl stearate, myristyl myristate, decyl oleate, cetyl lactate, myristyl lactate, isocetyl stearate, isocetyl isostearate, lanoline acetate, ethyl acetate, butyl acetate, oleic acid oil, cetostearyl alcohol, diisobutyl adipate, diisopropyl sebacate, di-2-ethyhexyl sebacate, 2-hexyldecyl myristate, 2-hexyldecyl palmitate and 2-hexyldecyl adipate.

The said silicon is prepared with such material as methyl polysiloxane, methylphenyl polysiloxane, methyl hydrogen polysiloxane, decamethyl polysiloxane and tetramethyl tetrahydrogen polysiloxane.

The said oil and fat are prepared with such material as avocado oil, camellia oil, turtle oil, macadamia nut oil, corn oil, mink oil, olive oil, rape seed oil, sesame oil, castor oil, linseed oil, safflower oil, jojoba oil, germ oil, coconut oil, palm oil and hydrogenated castor oil.

Among these oil ingredients, one to be liquid under room temperature and have carbon number of 10 or more and a flash point of 60° C. or higher, preferably 70° C. or higher, more preferably 80° C. or higher, is preferable in point of safety against fire.

The said oil ingredient is contained in the concentrate at 30 to 90 wt %, preferably 35 to 90 wt %. In case of the said oil ingredient of 30 wt %, when the aerosol composition is sprayed, the effective ingredient can not be effectively attached to objective oleophilic surfaces, thereby causing insufficient effect of the effective ingredient. On the other hand, in case of the said oil ingredient exceeding 90 wt %, a flash point occurs in the concentrate, so that the safety against fire becomes lower.

The said polyol is a ingredient not only to help the phases of the said oil ingredient and water uniform by using dimethyl ether, but also to eliminate the flash point from the concentrate to increase the safety against fire.

Specifically such polyol is prepared with one of the following materials: diol such as ethylene glycol propylene glycol and 1,3-butylene glycol triol such as glycerin and trimethylol propane; tetraol such as pentaerythritol; pentaol such as xylitol; hexaol such as sorbitol and mannitol; polymer of polyol such as diethylene glycol dipropylene ethylene glycol, triethylene glycol, polypropylene glycol, diglycerine, polyethylene glycol and triglycerine; alcohol alkyl ether such as ethylene glycol monomethyl ether, ethylene glycol monobutyl ether, ethylene glycol monophenyl ether, ethylene glycol monohexyl ether, ethylene glycol isopropyl ether, ethylene glycol dimethyl ether, diethylene glycol monoethyl ether, diethylene glycol monobutyl ether, triethylene glycol monoethyl ether, propylene glycol monoethyl ether, dipropylene glycol ethyl ether and diethylene glycol dimethyl ether; and alcohol ether ester such as ethylene glycol monoethyl ether acetate, diethylene glycol monoethyl ether acetate, propylene glycol monoethyl ether acetate and propylene glycol monopropyl ether acetate. Among these polyols, one with a flash point higher than that of the said oil ingredient is preferable, specifically one with a flash point of 90° C. or higher, more specifically 100° C. or higher, is preferable.

The said polyol is contained in the concentrate at 5 to 50 wt %, preferably 10 to 45 wt %. In case of the said polyol less than 5 wt % in the concentrate, a uniform aerosol composition can not obtained, while, in case of the said polyol higher than 50 wt %, drying characteristic becomes worse thereby to lower the usability.

As the said water, in addition to purified water, ion exchange water, distilled water and the like, buffer solutions described in Japanese Examined Patent Publication 1995-68092 such as ammonium benzoic acid-sodium hydroxide buffer, sodium benzoic acid-benzoic acid buffer, ammonium benzoic acid-ammonium buffer, ammonium benzoic acid-benzoic acid buffer and sodium carbonate-sodium acid carbonate buffer may be used. The said water is contained in the concentrate at 1 to 40 wt %, preferably 2 to 30 wt %. In case of the said water less than 1 wt % in the concentrate, a flash point occurs thereby to lower the safety against fire. On the other hand, in case of the said water higher than 40 wt %, the drying characteristic becomes worse, as well as making the effective ingredient difficult to attach effectively, resulting in lowering its efficacy. In addition, the solubility of the concentrate into the propellant becomes worse, and hence the aerosol composition can not be kept uniform.

The said effective ingredient is contained in the concentrate at 0.1 to 20 wt %, preferably 0.1 to 10 wt %. In case of the said effective ingredient less than 0.1%, the concentration of the effective ingredient contained in the aerosol composition becomes lower, and thus more amount of the composition is required to be sprayed in order to spray a necessary amount of the effective ingredient. On the other hand, in case of the effective ingredient higher than 20 wt %, the concentration of the effective ingredient becomes higher, and thus, in consideration of affect on living bodies, a method for decreasing the spray amount, such as making a diameter of a valve hole and a spray button hole smaller, is required. As a result, when sprayed, the aerosol composition can not be effectively dispersed in a wide range.

The said effective ingredient is prepared with one of the following materials: an insecticide such as phthalthrin, imiprothrin, allethrin, permethrin, cismethrin, proparthrin, resmethrin, d-phenothrin, tefluthrin, benfluthrin, neopinamin forte and chrysron forte; a insecticide efficacy enhancer such as Synepirin, piperonyl butoxide and octachlorocyclodipropyl ether; repellent such as N,N-diethyl-m-toluamide (deet, diethyl amide caprylate and dimethyl phthalate; deodorant such as lauryl methacrylate, geranyl crotonate, acetophenon myristate, benzyl acetate, benzyl propionate, methyl benzoate and methyl phenyl acetate; antibacterial agent such as benzalkonium chloride and benzethonium chloride, and a fragrance.

The aerosol composition according to the present invention may contain, other than the said essential ingredients, various ingredients such as lower alcohol, higher alcohol, a surfactant, a higher fatty add, wax and powder in the range not to allow the concentrate to have any flash point.

The said lower alcohol is an additional ingredient to help improve the drying characteristic in spraying and to uniformly dissolve the concentrate where the hydrophilic ingredient separates from the oleophilic ingredient by using dimethyl ether. The lower alcohol is prepared with monovalent alcohol having carbon numbers of 2 to 3, specifically, ethanol, propanol, isopropanol and the like.

The said higher alcohol is prepared with linear alcohol such as lauryl alcohol, cetyl alcohol, stearyl alcohol, behenyl alcohol, myristyl alcohol and oleyl alcohol, and branched alcohol such as monostearyl glycerol ether, lanolin alcohol, hexyl dodecanol, isostearyl alcohol and octyl dodecanol.

The said surfactant is prepared with such material as sorbitan fatty add ester, glycerin fatty add ester, decaglycerin fatty add ester, polyglycerin fatty acid ester, polyoxy ethylene sorbitan fatty add ester, polyoxy ethylene sorbitol fatty add ester, polyoxy ethylene glycerin fatty acid ester, polyoxy ethylene glycol fatty add ester, polyoxy ethylene alkyl ether, polyoxy ethylene polyoxy propylene alkyl ether, polyoxy ethylene alkyl phenyl ether, polyoxy ethylene castor oil/hydrogenated castor oil, polyoxy ethylene lanoline/lanoline alcohol/a beeswax derivative, polyoxy ethylene alkyl amine/fatty add amide.

The said higher fatty acid is prepared with such material as lauric add, myristic add, palmitic add, stearic add, behenic acid, oleic aid, isostearic add, linolic add, linoleic add, eicosapentaenoic acid (EPA) and Docosa Hexaenoic add (DHA).

The said wax is prepared with such material as beeswax, lanoline, lanoline acetate, candelilla wax, Carnauba wax, spermaceti wax and montan wax.

The said powder is prepared with one of the following materials: inorganic powders such as talc, kaolin, mica, sericite, magnesium carbonate, calcium carbonate, diatomaceous earth, magnesium silicate, calcium silicate, aluminium silicate, silica, zeolite, calcium sulfate, hydroxyapatite, ceramic powder, boron nitride and molybdenum disulfide; organic powders such as polyamide resin powder, polyethylene powder, polystyrene powder, polymethyl methacrylate powder, cellulose powder and silicon resin powder; inorganic pigments such as titanium dioxide, iron oxide, yellow oxide, titanium oxide, carbon black and ultramarine blue; and metal powder pigment such as aluminium powder and copper powder.

As the said propellant, dimethyl ether is used in a range from 90 to 49 wt %, preferably 80 to 45 wt %, in the aerosol composition. In other words, the concentrate is used in a range from 10 to 60 wt %, preferably 20 to 55 wt %, in the aerosol composition. When dimethyl ether exceeds 90% of the total amount, the compounding ratio of the necessary effective ingredient becomes less, resulting in impractical use. On the other hand, when it is less than 40%, no uniform composition can be obtained and the composition is sprayed in excessively large particle. This result is not preferable.

The above aerosol composition is preferably sprayed in 0.1 to 2.0 g/second, more preferably 0.1 to 1.5 g/second. In case of a sprayed amount less than 0.1 g/second, it takes a longer time to spray until a necessary amount of the effective ingredient is sprayed, so that the effective ingredient may be inhaled by a human body during this period. On the other hand, in case of a sprayed amount more than 2.0 g/second, a flame length becomes longer in a flame length test to make the safety against fire worse. Now in Japan, flammability is not classified based on a flame length. However, it is preferable to make a flame length to a length less than 45 cm, the condition of the weak flammability.

Figure 1:
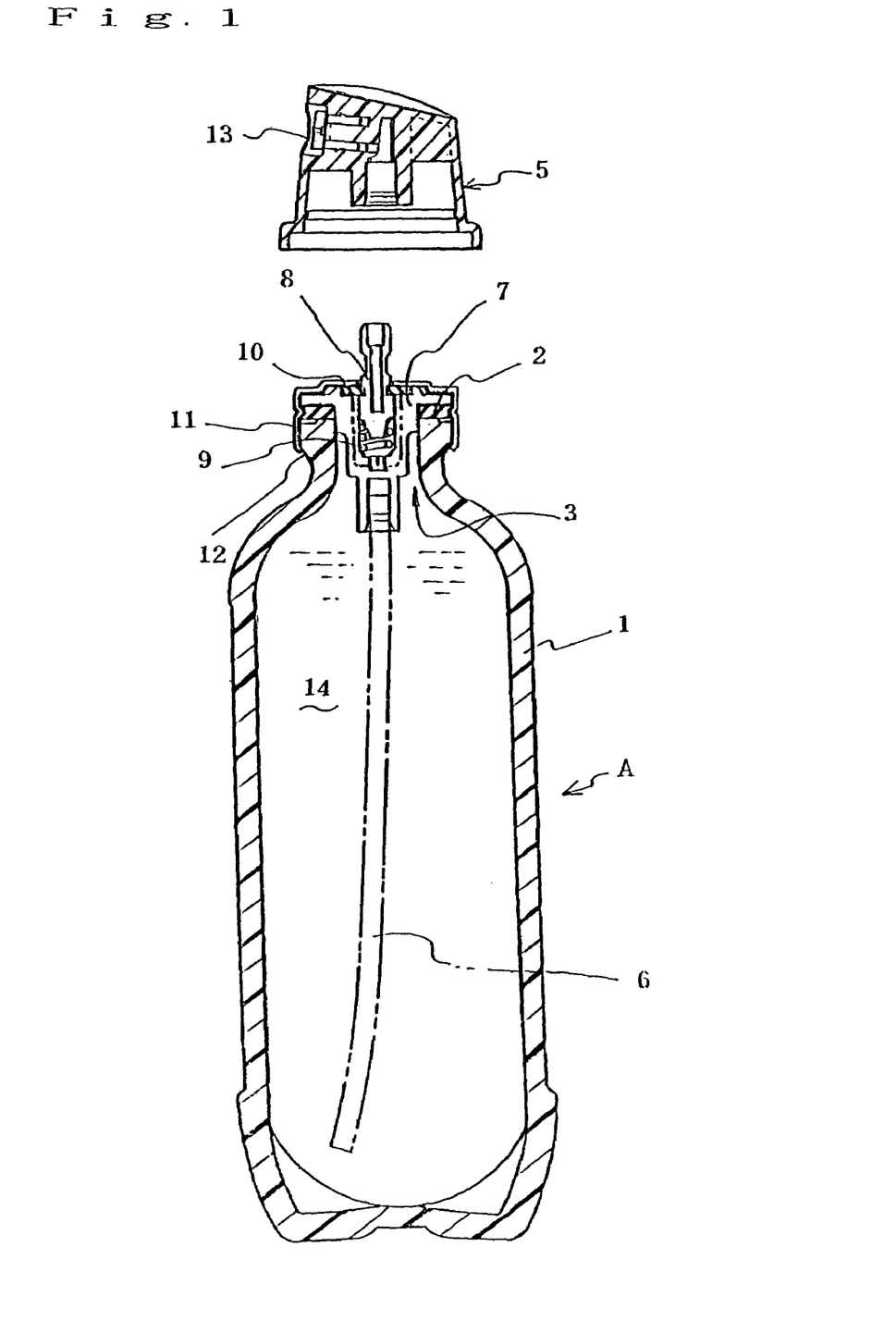
FIG. 1 is a sectional view showing an embodiment of a container to fill the aerosol composition according to the present invention.

The above aerosol composition is prepared as an aerosol product by filling in an aerosol container A made from a synthetic resin, for example shown in FIG. 1. The aerosol container A comprises a cylindrical main body 1 with a bottom, a valve 3 attached to an opening on the top end of the main body 1 through a gasket 2, and a push button 5. Reference numeral 6 denotes a dip tube.

The main body 1 is made of thermoplastic resin difficult to be corroded and easy to be formed, such as polyethylene terephthalate (PET), polybutylene terephthalate (PBT), polyacrylonitrile (PA), Barex, by extrusion molding or blow molding, for example. The valve 3 comprises a resin-made valve housing 7, a stem 8 housed in the inside thereof so as to be movable vertically, a spring 9 energizing upward the stem 8 continuously, a stem rubber 10 fitted around the stem 8 and fixed to the valve housing 7, and a mounting cup (cover) 11 to fit these parts integrally to the main body 1. The valve housing 7 and the stem 8 are made of thermoplastic resin such as nylon or Duracon. The mounting cup 11 is made of a metal sheet formed in a shape of a cylinder with a bottom and fixes the valve 3 tightly to the main body 1 normally by crimping its bottom end onto a step portion 12 on the lower mouth part of the main body 1. The said push button 5 is also made of synthetic resin, and to its front surface, a nozzle 13, conventionally and publicly known for spray use, is attached.

In the above aerosol container A, 2 solutions of an A solution consisting of a mixture of diethylene glycol monoethyl ether acetate and purified water, and a B solution consisting of kerosine containing an effective ingredient such as an insecticide, are separately dispensed. Then, the valve 3 is attached, dimethyl ether is filled from the stem 8, and finally, the push button 5 is attached to complete an aerosol product.

The inner face of the main body 1, contacting with an aerosol composition 14, and the valve 3 are made of the synthetic resin, and therefore, this product is not corroded by the content matter, regardless of containing water in the aerosol composition. In addition, it is not corroded also by the effective ingredient to allow containing the effective ingredient safely.

Figure 2:
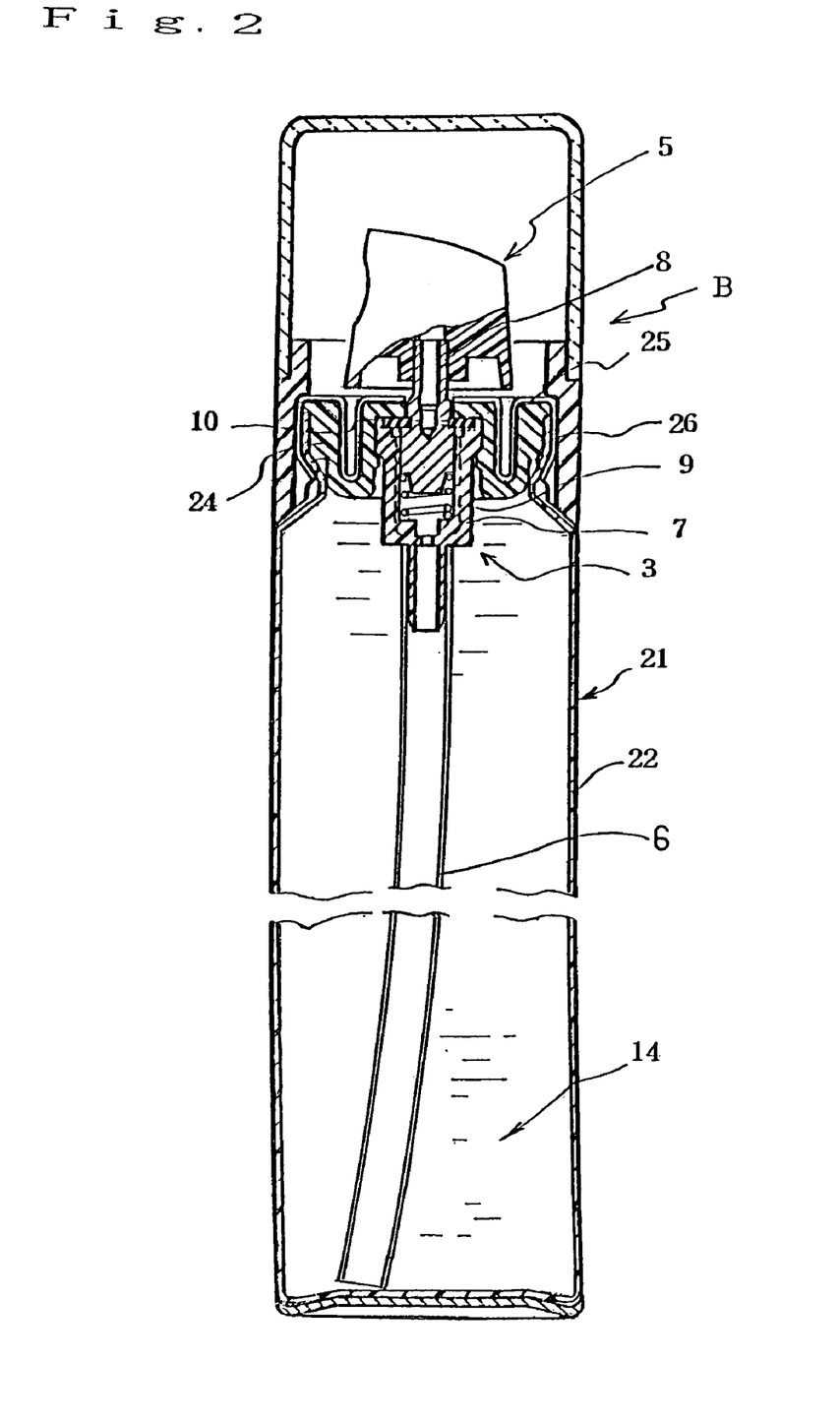
FIG. 2 is a sectional view showing a further embodiment of a container to fill the aerosol composition according to the present invention.

An aerosol container B shown in FIG. 2 comprises a main body 21 of the container, a synthetic resin-made internal bag liner) 22 with anticorrosive ability against an aerosol composition contained in the inside so as to lap over, the valve 3 attached to the opening portion of the top ends of them, and the push button 5 attached to the valve.

The main body 21 can be formed by formed by a metal sheet such as aluminium, tinplate or steel, in a cylindrical shape with a bottom. The main body 21 itself does not need anticorrosive ability against the aerosol composition, and thereby can be made of any metal and may be made of synthetic resin. The said internal bag 22 may be same as that used for a double aerosol product, where the concentrate and the propellant are separately filled in the container. No space is required between the internal bag 22 and the main body 21 as the internal bag 22 contacts closely to the inner face of the main body 21 after the aerosol composition filled in.

The valve 3 comprises the valve housing 7 made of synthetic resin, the stem 8 housed vertically movable in the inside thereof, the spring 9 energizing upward the stem continuously, the stem rubber 10 fitted around the stem 8 and fixed to the valve housing 7, a mounting cup 24 made of synthetic resin to fit these parts integrally to the main body 21, and a cover 25 made of a metal sheet.

The synthetic resin composing the said internal bag 22 is prepared with, for example, a layered body with a single layer or a double or more layers such as linear low density polyethylene (LLDPE), low density polyethylene (LDPE), polypropylene (PP), polyethylene terephthalate (PET), polybutylene terephthalate (PBT), polyethylene naphthalate (PEN), polyacrylonitrile (PAN), ethylene vinyl alcohol copolymer (EVOH), nylon (NY) and the like. For example, a triphasic-layered film made from LDPE/EVOH/LDPE can be used. The internal bag 22 is ordinarily formed by blow molding. The thickness of the internal bag 22 normally ranges from 0.1 to 2.0 mm, preferably from 0.3 to 1.0 mm.

Around the top end of the main body 21, the step part 26 is provided to engage the mounting cup 24. The mounting cup 24 is inserted into the opening of the top end of the main body 21 in a state of holding the top end of the internal bag 22 between the mounting cup 24 and the step portion 26, and attached by crimping the bottom end of the cover 25 from the outside of the main body 21 to the lower part of the step portion 26.

In this container, the aerosol composition is filled, as in the case of FIG. 1, to complete an aerosol product. In this product, the aerosol composition only contacts to the parts with anticorrosive property against the aerosol composition, such as the internal bag 22, the valve housing 7 and the mounting cup 24, and therefore, corrosion of the container and denaturation of the aerosol composition are prevented.

Figure 3:
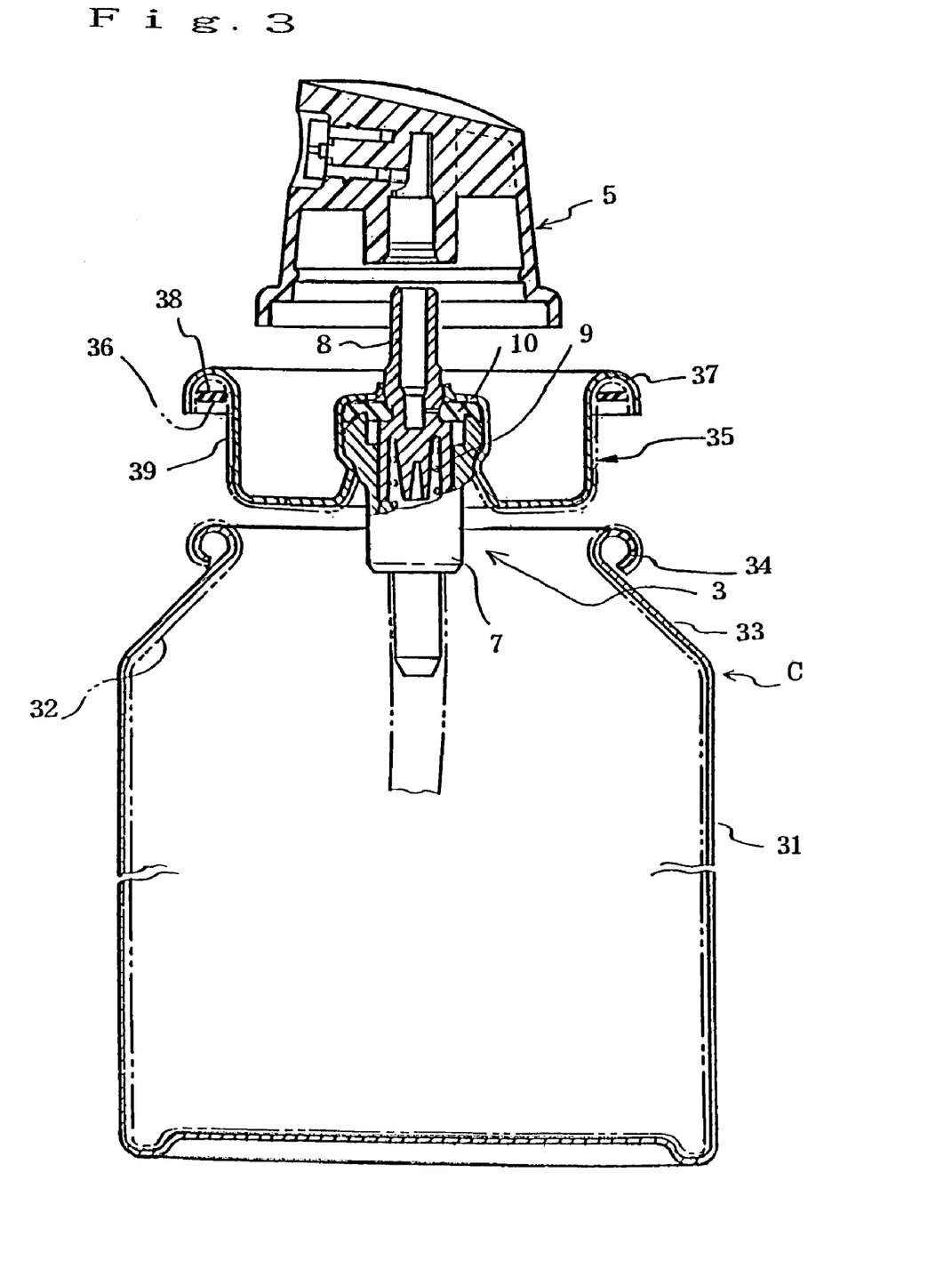
FIG. 3 is a sectional view showing a still further embodiment of a container to fill the aerosol composition according to the present invention.

An aerosol container C shown in FIG. 3 comprises a main body 31 of the container, the valve 3 attached to the opening of the top end thereof, and the push button 5 attached to the valve 3. The main body 31 is obtained by forming a laminated sheet material, made of a metal sheet such as aluminium, tinplate or steel and a synthetic resin film 32 laminated in the side of the inner face of the container, in a shape of cylinder with a bottom, and by providing a shoulder portion 33 made by draw forming and a bead portion 34 made by curling forming. The metal sheet requires no anticorrosive property against the aerosol composition, and therefore, any metal can be used and synthetic resin may also be used.

A material of the synthetic resin film 32 can be a polyolefin such as polyethylene and polypropylene, a polyamide such as nylon 6, nylon 6,6, nylon 11, and nylon 12, and a polyester such as polyethylene terephthalate and polybutylene terephthalate. The thickness of the synthetic resin film 32 ranges preferably from 5 to 300 μm, particularly from 10 to 100 μM.

The valve 3 comprises the synthetic resin-made valve housing 7, the stem 8 housed in the inside thereof movably vertically, the spring 9 energizing upward the stem continuously, the stem rubber 10 fitted around the stem 8 and fixed to the valve housing 7, and a mounting cup 35 to fit these parts integrally to the main body. The mounting cup 35 is made, similarly to the main body 31, of a laminated material composed of a metal thin plate and a synthetic resin film 36 and the synthetic resin film 36 is positioned in the internal side of the container.

The mounting cup 35 holds the valve housing 7 in its central part and has a flange portion at its peripheral part in a U shape in a sectional view so as to cover the bead part of the main body 31. The above-described valve 3 is fixed to the main body 31 by fitting the mounting cup 35 to the opening of the top end of the main body 31 and crimping an erect wall 39 thereof to the inner face of the shoulder portion 33 of the main body of the container.

In this container, the aerosol composition is filled, as in the case of FIG. 1, to complete an aerosol product. In addition, the metal sheet of the main body is protected by the synthetic resin film, and therefore, corrosion of the container and denaturation of the content are prevented.

Figure 4:
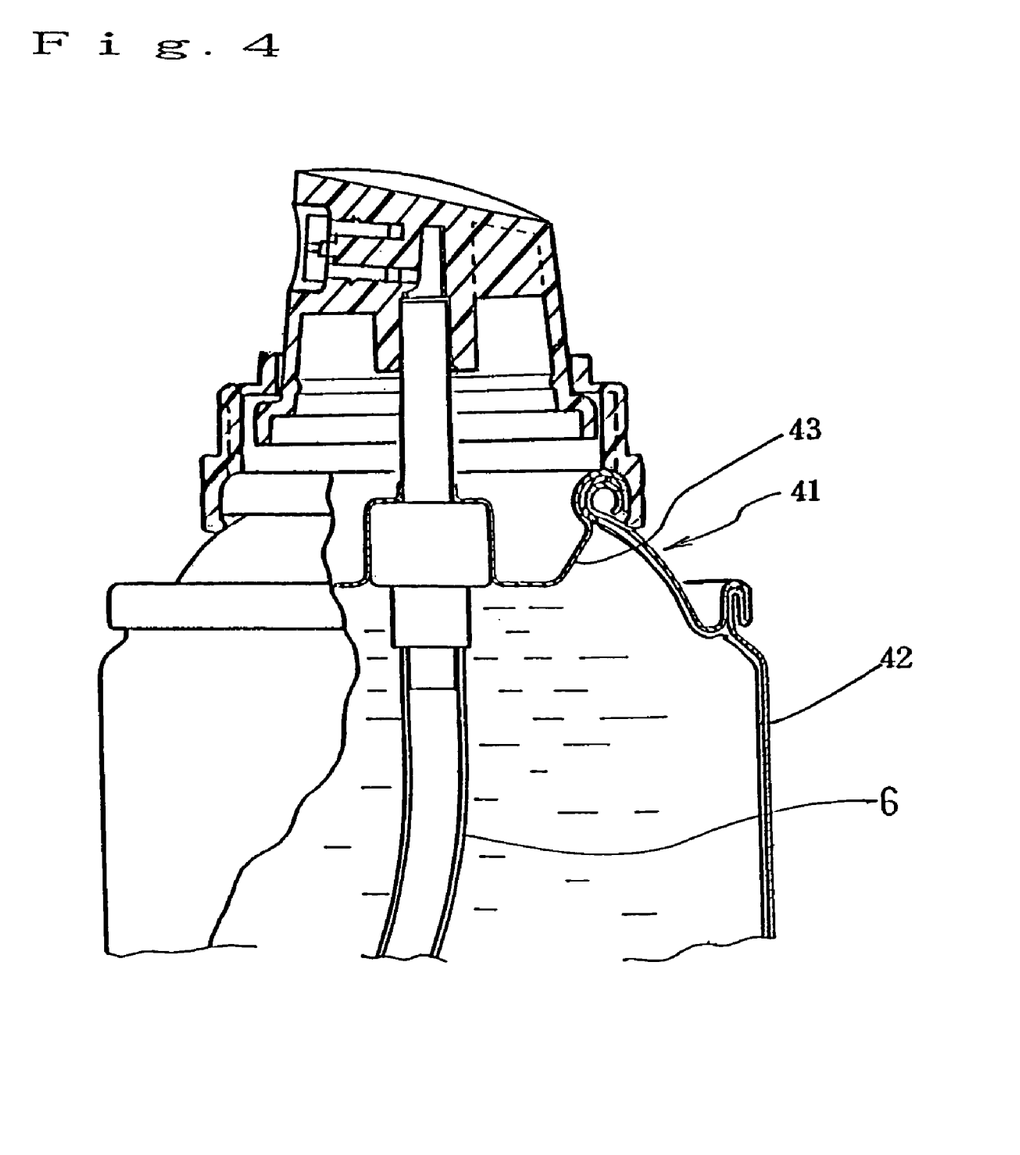
FIG. 4 is a sectional view showing another embodiment of a container to fill the aerosol composition according to the present invention.

For reference, in replacing to the synthetic resin film in FIG. 3, as shown in FIG. 4, a main body 41 of a container may be provided with a synthetic resin coat film 42 on its inner face. In this case, on the inner face side of the main body 41 previously formed with such metal sheet as tinplate, the thermosetting resin such as epoxy resin, polyester resin, acrylic resin and epoxy ester resin can be used as a coat film by electrostatic or powder coating. The thickness of the coat film preferably ranges from 10 to 100 μn and a grain of a coating ranges from 25 to 80 μm. It may also be made on the inner face of a mounting cup 43.

Consequently, in case of a metal-made container, a synthetic resin internal bag, a film or a coated film is provided on the inner face thereof to protect the container so that an electric current is zero, thereby to safely contain the aerosol composition even containing water.

EXAMPLE

The aerosol composition according to the present invention is described as follows with reference to specific examples.

*Safety Against Fire

1. Measurement of the Flash Point of the Concentrate.

Under Article 1 Paragraph 6, Decree Law with regard to regulation of hazardous materials, the flash points of the concentrates shown in Table 1 were measured by using a tag closed-type flash point tester in the range from a room temperature to 80° C. In case of a flash point under 80° C., measurement was carried out by using a Cleveland open-type flash point tester. The results are shown in Table 2.

TABLE 1

| | | <Concentrate> | | | | |
|---|---|---|---|---|---|---|
| | | Concentrate 1 | Concentrate 2 | Concentrate 3 | Concentrate 4 | Concentrate 5 |
| Composition | Kerosene | 70.0 | 87.0 | 87.0 | 100.0 | 92.0 |
| | Diethylene glycol monoethyl ether acetate | 25.0 | 10.0 | — | — | — |
| | Diethylene glycol | — | — | 10.0 | — | 5.0 |
| | Purified water | 5.0 | 3.0 | 3.0 | — | 3.0 |
| Total | | 100.0 | 100.0 | 100.0 | 100.0 | 100.0 |
| Appearance | | Separated | Separated | Separated | Uniform | Separated |
| | | | | | | (Wt %) |

TABLE 2

| <Test results> | |
|---|---|
| | Flash point (° C.) |
| Concentrate 1 | Not observed |
| Concentrate 2 | Not observed |
| Concentrate 3 | Not observed |
| Concentrate 4 | 94.0 |
| Concentrate 5 | 98.2 |

2. Flame Length Test

The aerosol compositions shown in Table 3 were filled in the containers under the following material specification, to manufacture aerosol products by attaching valves and spray buttons shown in Table 4. The obtained products were kept at 25° C. and sprayed toward a flame (length of 5 cm) in a distance of 15 cm so as to pass through a ⅓ of the top part of the flame. The results are presented in Table 5. The concentrate 1 to 3 were used to prepare the aerosol compositions of examples 1 to 3 and the concentrate 4 was used to prepare the aerosol compositions of comparative examples 1 and 2.

TABLE 3

<Aerosol compositions>

| | | Example 1 | Example 2 | Example 3 | Comparative example 1 | Comparative example 2 |
|---|---|---|---|---|---|---|
| Composition | Concentrate | 30.0 (Concentrate 1) | 30.0 (Concentrate 2) | 30.0 (Concentrate 3) | 30.0 (Concentrate 4) | 30.0 (Concentrate 4) |
| Propellant | DME | 70.0 | 70.0 | 70.0 | 70.0 | — |
| | LPG | — | — | — | — | 70.0 |
| Total | | 100.0 | 100.0 | 100.0 | 100.0 | 100.0 |
| Appearance | | Uniform | Uniform | Uniform | Uniform | Uniform |
| | | | | | | (Wt %) |

<Material Specification>

Container: tinplate pressure-proof container (electrostatically coated with polyester resin on the inner face of the container in FIG. 4. Film thickness is 50 μm.)

Valve and spray button: Table 4.

TABLE 4

| | Specification 1 | Specification 2 | Specification 3 |
|---|---|---|---|
| Stem hole | ⌀0.3 | ⌀0.4 | ⌀0.5 |
| Housing Bottom hole | ⌀0.8 | ⌀0.8 | ⌀0.8 |
| Side hole | ⌀0.35 | ⌀0.35 | ⌀0.35 |
| Spray button | ⌀0.4 | ⌀0.4 | ⌀0.4 |

TABLE 5

<Test results>

| Concentrate | Valve | Flame length | |
|---|---|---|---|
| Example 1 | Specification 1 | 20 cm | No back fire |
| | Specification 2 | 25 cm | No back fire |
| | Specification 3 | 30 cm | No back fire |
| Example 2 | Specification 1 | 25 cm | No back fire |
| | Specification 2 | 25 cm | No back fire |
| | Specification 3 | 30 cm | No back fire |
| Example 3 | Specification 1 | 25 cm | No back fire |
| | Specification 2 | 25 cm | No back fire |
| | Specification 3 | 30 cm | No back fire |
| Comparative example 1 | Specification 1 | 35 cm | No back fire |
| | Specification 2 | 40 cm | No back fire |
| | Specification 3 | 45 cm | No back fire |
| Comparative example 2 | Specification 1 | 70 cm | No back fire |
| | Specification 2 | 80 cm | No back fire |
| | Specification 3 | 90 cm | No back fire |

3. Explosion Test (Measurement of Lower Limit Explosion Concentration)

<Test Equipment>

A horizontal cylindrical container having an internal volume of 50 L (liter) was used. The container comprises a sample blow-in mouth on the one end thereof, a lid on the other end freely openable by a pressure of explosion occurred in the container, a fan to agitate aerosol blown in, and a ignition.

<Last Method>

The interior temperature of the container was kept at 25° C. and the fan was rotated, while a switch of the ignition plug was turned on to spray the sample for 1 second and stop for 2 seconds alternately and repeatedly. A weight of the sample consumed up to explosion was measured and then, the lower limit explosion concentration (Ec) was calculated on the basis of the following formula. For reference, the temperature of the sample was 25° C.

$$Ec = \frac{W1 - W2}{V} \quad \text{[Math. Formula 1]}$$

Where,

Ec: lower limit explosion concentration (g/L)

V: internal volume of test equipment (L)

W1: weight of sample before spraying (g)

W2: weight of sample after spraying (g)

<Test Sample>

The aerosol compositions of the examples 1 to 3 and comparative examples 1 and 2 in Table 3.

TABLE 6

<Test results>

| | Ec |
|---|---|
| Example 1 | 0.17 |
| Example 2 | 0.14 |
| Example 3 | 0.15 |
| Comparative example 1 | 0.12 |
| Comparative example 2 | 0.10 |

From the test results in the above Table 2, the concentrates 1 to 3 used for the aerosol compositions according to the present invention have no flash point, while the concentrate 4 consisting of only kerosene has the flash point at 94.0° C. The concentrate 5 also has the flash point at 98.2° C., and therefore was not used as the comparative example. In addition, the products (the examples 1 to 3), made by aerosolizing the concentrates 1 to 3 using dimethyl ether, showed the flame lengths ranging 20 to 30 cm as shown in FIG. 5, and the flame lengths are very short in comparison with the product (comparative examples 1 and 2) made by aerosolizing the concentrate 4. As for the comparative example 1, some flame lengths reached 45 cm depending on the diameters of the valve holes, so that the diameter of the valve hole is required to be downsized to satisfy the weak flammability condition. In addition, from Table 6, the lower limit explosion concentration of the examples 1 to 3 is as high as 0.14 to 0.17 (g/L) and conforms to the classification for the weak flammability according to the former Ministry of International Trade and Industry Notice No. 557 (Oct. 15, 1965) and thus, showing higher safety against fire.

<Formulation Example>

For the concentrate compositions in Tables 7 to 10, the appearance and ignitability tests were carried out in the same method as described previously. The results are presented in Table 11. In addition, those were mixed with dimethyl ether to obtain aerosol products.

TABLE 7

Insecticide for space

|  | Formulation 1 | Formulation 2 |
|---|---|---|
| Concentrate composition |  |  |
| Kerosene (Neothiosol:brand name) | 69.4 | 86.4 |
| Diethylene glycol monoethyl ether acetate | 25.0 | 10.0 |
| Purified water | 5.0 | 3.0 |
| Permethrin | 0.5 | 0.5 |
| Synepirin | 0.1 | 0.1 |
| Total | 100.0 | 100.0 |
|  | (Wt %) |  |
| Aerosol composition |  |  |
| The above concentrate | 25.0 | 30.0 |
| Dimethyl ether | 75.0 | 70.0 |
| Total | 100.0 | 100.0 |
|  | (Wt %) |  |

TABLE 8

Insecticide for cockroach

|  | Formulation 3 | Formulation 4 |
|---|---|---|
| Concentrate composition |  |  |
| Kerosene (Neothiosol) | 67.0 | 84.0 |
| Diethylene glycol | 25.0 | 10.0 |
| Purified water | 5.0 | 3.0 |
| d-phenothrin | 1.0 | 1.0 |
| Octachlorodipropyl ether | 2.0 | 2.0 |
| Total | 100.0 | 100.0 |
|  | (Wt %) |  |
| Aerosol composition |  |  |
| The above concentrate | 25.0 | 30.0 |
| Dimethyl ether | 75.0 | 70.0 |
| Total | 100.0 | 100.0 |
|  | (Wt %) |  |

TABLE 9

Insecticide for space

|  | Formulation 5 | Formulation 6 | Formulation 7 | Formulation 8 |
|---|---|---|---|---|
| Concentrate composition |  |  |  |  |
| Kerosene (Neothiosol) | 44.5 | 39.5 | 86.6 | 86.6 |
| Dipropylene glycol | 40.0 | 40.0 | 10.0 | — |
| Triethyl phosphate | — | — | — | 10.0 |
| Purified water | 15.0 | 20.0 | 3.0 | 3.0 |
| Neopinamin forte | 0.4 | 0.4 | 0.3 | 0.3 |
| Chrysron forte | 0.1 | 0.1 | 0.1 | 0.1 |
| Total | 100.0 | 100.0 | 100.0 | 100.0 |
|  |  |  |  | (Wt %) |
| Aerosol composition |  |  |  |  |
| The above concentrate | 25.0 | 25.0 | 35.0 | 35.0 |
| Dimethyl ether | 75.0 | 75.0 | 65.0 | 65.0 |
| Total | 100.0 | 100.0 | 100.0 | 100.0 |
|  |  |  |  | (Wt %) |

TABLE 10

Insecticide for cockroach

|  | Formulation 9 | Formulation 10 |
|---|---|---|
| Concentrate composition |  |  |
| Imiprothrin | 3.6 | 3.6 |
| Isopropyl myristate | 53.1 | 31.9 |
| Kerosene | — | 21.2 |
| Dipropylene glycol | 28.9 | 28.9 |
| Purified water | 14.4 | 14.4 |
| Total | 100.0 | 100.0 |
|  |  | (Wt %) |
| Aerosol composition |  |  |
| The above concentrate | 25.0 | 25.0 |
| Dimethyl ether | 75.0 | 75.0 |
| Total | 100.0 | 100.0 |
|  |  | (Wt %) |

The above aerosol compositions were filled in the container comprising the valve and button as described below to be as an aerosol product, and a flame length test and an explosibility test were carried out in the same method as described previously. The results are presented in Table 11.

<Material Specification>

Container: tinplate pressure-proof container (electrostatically coated with polyester resin on the inner face of the container in FIG. 4. Film thickness is 50 μm.)

Valve: stem hole 0.4 mm, a bottom hole on a housing 0.8 mm, side hole 0.35 mm.

Spray button diameter: 0.4 mm.

TABLE 11

<Test results>

|  |  | Formulation 1 | Formulation 2 | Formulation 3 | Formulation 4 |
|---|---|---|---|---|---|
| Charac- teristics of con- | Appearance | Separated | Separated | Separated | Separated |
|  | Flash point | Not observed | Not observed | Not observed | Not observed |

TABLE 11-continued

| centrate | | <Test results> | | | |
|---|---|---|---|---|---|
| Characteristics of aerosol | Appearance<br>Flame length<br>Ec | Uniform<br>25 cm<br>0.16 | Uniform<br>25 cm<br>0.14 | Uniform<br>25 cm<br>0.16 | Uniform<br>25 cm<br>0.14 |
| | | Formulation 5 | Formulation 6 | Formulation 7 | Formulation 8 |
| Characteristics of concentrate | Appearance<br>Flash point | Separated<br>Not observed | Separated<br>Not observed | Separated<br>Not observed | Separated<br>Not observed |
| Characteristics of aerosol | Appearance<br>Flame length<br>Ec | Uniform<br>25 cm<br>0.17 | Uniform<br>20 cm<br>0.18 | Uniform<br>30 cm<br>0.18 | Uniform<br>35 cm<br>0.17 |
| | | Formulation 9 | Formulation 10 | | |
| Characteristics of concentrate | Appearance<br>Flash point | Separated<br>Not observed | Separated<br>Not observed | | |
| Characteristics of aerosol | Appearance<br>Flame length<br>Ec | Uniform<br>25 cm<br>0.19 | Uniform<br>30 cm<br>0.18 | | |

(Note) No back fire is observed in any flame length.

As known from Table 11, on the basis of the ignitability test, all the concentrates have no flash point and do not fit the hazardous matter. In addition, on the flame length test, the products prepared by aerosolizing the concentrates using dimethyl ether had the flame lengths from 20 to 35 cm and on the explosibility test, the lower limit explosion concentration ranged from 0.14 to 0.19, resulting in the classification for the weak flammability. From these results, it is proven that the products are high in safety against fire.

4. Test in a Time Sequence

The aerosol compositions of the above formulation 1 to 10 were filled according to the following material specification and the manufacturing method to obtain aerosol products.

TABLE 12

| | <Material specification> | |
|---|---|---|
| Specification | Container | Valve |
| 1 | Polyethylene terephthalate-made container (FIG. 1) | Valve with a Duracon-made housing |
| 2 | Aluminium container, inserted a polyethylene-made internal bag with the thickness of 0.5 mm in its interior (FIG. 2) | Valve with a mounting cup and a nylon-made housing |
| 3 | Aluminium container coated by laminating with a polyethylene terephthalate in thickness of 15 μm on the inner face (FIG. 3) | Valve coated by laminating with a polyethylene terephthalate on the inner face of an aluminium-made mounting cup |
| 4 | Tinplate-made container electrostatically coated with a polyester resin (resin film thickness of 50 μm) on the inner face (FIG. 4) | Valve coated by laminating a polypropylene on the both faces of tinplate-made mounting cup |

<Manufacturing Method>

As for the specifications 1 and 2, each concentrate was filled in each container and each valve was fitted thereto. Then, dimethyl ether was filled from each stem, and thereby to obtain aerosol products. As for the specifications 3 and 4, each concentrate was filled in each container and dimethyl ether was filled by under cup filling. Then, each aerosol valve was fitted thereto, and thereby to obtain aerosol products.

<Test Condition>

For the specification 1, the aerosol products were kept under 35° C. for 8 months, while for the specifications 2, 3 and 4, under 45° C. for 3 months, in erect and inverted states for all. The test results are presented in Tables 13, 14 and 15.

TABLE 13

| | | | <Test result> | | | |
|---|---|---|---|---|---|---|
| | | Material | Property of concentrate | | Evaluation at opening | |
| | Concentrate | specification | Appearance | Smell | Container | Valve |
| Insecticide for space | Formulation 1 | 1 | A | A | A | A |
| | | 2 | A | A | A | A |
| | | 3 | A | A | A | A |
| | | 4 | A | A | A | A |
| | Formulation 2 | 1 | A | A | A | A |
| | | 2 | A | A | A | A |
| | | 3 | A | A | A | A |
| | | 4 | A | A | A | A |
| Insecticide for cockroach | Formulation 3 | 1 | A | A | A | A |
| | | 2 | A | A | A | A |
| | | 3 | A | A | A | A |
| | | 4 | A | A | A | A |
| | Formulation 4 | 1 | A | A | A | A |
| | | 2 | A | A | A | A |
| | | 3 | A | A | A | A |
| | | 4 | A | A | A | A |

TABLE 14

| | | Material | Property of concentrate | | Evaluation at opening | |
|---|---|---|---|---|---|---|
| | Concentrate | specification | Appearance | Smell | Container | Valve |
| Insecticide for space | Formulation 5 | 1 | A | A | A | A |
| | | 2 | A | A | A | A |
| | | 3 | A | A | A–B | A |
| | | 4 | A | A | A–B | A |
| | Formulation 6 | 1 | A | A | A | A |
| | | 2 | A | A | A | A |
| | | 3 | A | A | A–B | A |
| | | 4 | A | A | A–B | A |
| | Formulation 7 | 1 | A | A | A | A |
| | | 2 | A | A | A | A |
| | | 3 | A | A | A | A |
| | | 4 | A | A | A | A |
| | Formulation 8 | 1 | A | A | A | A |
| | | 2 | A | A | A | A |
| | | 3 | A | A | A | A |
| | | 4 | A | A | A | A |

TABLE 15

| Concentrate | Material specification | Property of concentrate | | Evaluation at opening | |
|---|---|---|---|---|---|
| | | Appearance | Smell | Container | Valve |
| Insecticide for cockroach | Formulation 9 | | | | |
| | 1 | A | A | A | A |
| | 2 | A | A | A | A |
| | 3 | A | A | A–B | A |
| | 4 | A | A | A | A |
| | Formulation 10 | | | | |
| | 1 | A | A | A | A |
| | 2 | A | A | A | A |
| | 3 | A | A | A–B | A |
| | 4 | A | A | A | A |

Evaluation Standard

Property of concentrate: comparison of the concentrate before the start of the test in time sequence with the concentrate collected after use as a test sample.

A: no abnormality observed

C: very changed

Evaluation at Opening:

A: no abnormality observed

B: blister was observed in the resin layer, while no corrosion was observed on the surface of the metal C: corrosion observed on the surface of the metal.

As known from Tables 13 to 15, all the aerosol products showed no practical problem in keeping in erect and inverted states. Therefore, it can be proven that the compositions according to the formulations 1 to 10 are stable against to the container.

EFFECT OF THE INVENTION

The aerosol composition of the present invention contains an oil ingredient, polyol and water in a specific proportion in a concentrate, so that it has no flash point under 1 atmospheric pressure to be in higher safety against fire. In addition, the aerosol product has a uniform liquid composition, while on spraying, the oleophilic liquid containing the effective ingredient separates from the hydrophilic liquid. Therefore, the effective ingredient can attach effectively to the objective face for spraying, and hence, the effective ingredient never decreases its efficacy.

The invention claimed is:

1. A single phase propellant-concentrate aerosol composition for use in the spray application of an active ingredient from a pressurized container, consisting essentially of a first component (a) and a second component (b), wherein:
component (a) is a concentrate of 10 to 60 wt % of component (a) and component (b), the concentrate consisting essentially of
(i) an oil ingredient of 30 to 90 wt % of component (a),
(ii) polyol of 5 to 50 wt % of component (a),
(iii) water of 1 to 30 wt % of component (a), and
(iv) the active ingredient of 0.1 to 20 wt % of component (a); and
component (b) is a dimethyl ether propellant of 90 to 40 wt % of component (a) and component (b);
wherein the component (a) does not have a flash point under 1 atmosphere of pressure,
wherein the oil ingredient is selected from the group consisting of hydrocarbon, silicone, ester oil and the mixture, and the oil ingredient (1) is liquid under room temperature, (2) has a carbon number of 10 or more, and (3) has a flash point of 60° C. or higher,
wherein the polyol has a flash point of 100° C. or higher, and
wherein, when said aerosol composition is sprayed into the air from the pressurized container, said component (b) vaporizes in the air and said component (a) separates in the air into a hydrophilic liquid combination of polyol and water and an oleophilic liquid combination of the active ingredient and the oil ingredient.

2. A single phase propellant-concentrate aerosol composition according to claim 1, wherein the active ingredient is an insecticide.

3. A single phase propellant-concentrate aerosol composition according to claim 1, wherein a flash point of the polyol is higher than a flash point of the oil ingredient.

4. A single phase propellant-concentrate aerosol composition according to claim 1, wherein the oil ingredient is hydrocarbon.

5. A single phase propellant-concentrate aerosol composition according to claim 1, wherein the component (a) is a concentrate of 10 to 35 wt % of component (a) and component (b), and component (b) is dimethyl ether propellant of 90 to 65 wt % of component (a) and component (b).

6. A single phase propellant-concentrate aerosol composition according to claim 1, wherein the flash point of the oil ingredient is 60 to 100° C.

7. A single phase propellant-concentrate aerosol composition according to claim 1, wherein the oil ingredient is selected from the group consisting of Kerosene (Neothiosol), isopropyl myristate and the mixture.

8. A single phase propellant-concentrate aerosol composition according to claim 1, wherein the polyol is selected from the group consisting of diethylene glycol, diethylene glycol monoethyl ether acetate, and a mixture thereof.

* * * * *